United States Patent [19]

Turner et al.

[11] Patent Number: 5,483,014
[45] Date of Patent: Jan. 9, 1996

[54] CATALYSTS, METHOD OF PREPARING THESE CATALYSTS, AND POLYMERIZATION PROCESSES WHEREIN THESE CATALYSTS ARE USED

[76] Inventors: Howard W. Turner, 303 Elder Glen, Webster, Tex. 77598; Gregory G. Hlatky, 15900 Space Center, Houston, Tex. 77062

[21] Appl. No.: 301,163

[22] Filed: Sep. 6, 1994

Related U.S. Application Data

[60] Continuation of Ser. No. 123,400, Sep. 17, 1993, abandoned, which is a division of Ser. No. 875,165, Apr. 28, 1992, Pat. No. 5,278,119, which is a continuation of Ser. No. 133,052, Dec. 21, 1987, abandoned, which is a continuation-in-part of Ser. No. 11,471, Jan. 30, 1987, abandoned.

[51] Int. Cl.⁶ .............................. C08F 4/16; C08F 10/00
[52] U.S. Cl. ................. 526/113; 526/117; 526/120; 526/126; 526/131; 526/134; 526/352; 526/348.6
[58] Field of Search ....................... 526/113, 117, 526/120, 126, 131, 134, 352, 348.6

[56] References Cited

U.S. PATENT DOCUMENTS

| | | |
|---|---|---|
| 2,840,551 | 6/1958 | Field et al. . |
| 5,278,119 | 1/1994 | Turner et al. .................. 502/155 |

FOREIGN PATENT DOCUMENTS 681141  3/1964  Canada .

OTHER PUBLICATIONS

Long, J., Am. Chem. Soc. 81, (1959), 5312–5316.
Eisch et al., J. Am. Chem. Soc(1985), 107, 7219–7221.
Dyuchrovskii et al., Jour. Poly. Sci. Part C, No. 16, (1967)pp. 2333–2339.
Breslow et al., J. Am. Chem. Soc. (1959), vol. 81. 81, pp. 81–86.
Kinetics and Mechanisms of the Reaction of Aluminum Alkyls with Titanium Halides, A. K. Zefirova et al., (Translated from Doklady Akademii Nauk SSSR, vol. 136, No. 3, pp. 599–602 (1961).
Grigorvan et al., Vysokomol. soved. A9: No. 6, 1233–1237 (1967).
Belov et al., Die Makromollekulare Chemie, 140 (1970) 213–227 (No. 3415).
Jordan et al., J. Am. Chem. Soc. (1986), 108, 7410–7411.
Schmidt et al., J. Am. Chem. Soc. (1985), 107, 1443–1444.
Cracknell et al., J. Chem. Soc., Chem. Commun. (1984) 326–328.
Dyachkovskii, Coordination Polymerization, Academii Press, New York, 1975, pp. 199–223.
Abstract No. 314, Abstracts of the 193rd ACS National Meeting, Denver, Colo., Apr. 1987, Division of Inorganic Chemistry.
Bochmann et al., J. Chem. Soc. (1986), 108, 1718–1719.
Jordan et al., J. Am. Chem. Soc. (1986), 108, 1718–1719.
Long et al., J. Am. Chem. Soc., (1960), vol. 82, pp. 1953–1957.
D'Yachlovskii, Vyysokomol, soyed, 7: No. 1, 114–115 (1965).

*Primary Examiner*—Asok Pal

[57] ABSTRACT

A polymerization process for olefins, diolefins and/or acetylenically unsaturated monomers is described. The monomers are contacted with an ionic catalyst which comprises a cyclopentadienyl derivative of Group IV-B metals as cation and a compatible non-coordinating anion containing a plurality of boron atoms. Borate, carborate, borane, carborane, metallaborane and metallacarborane compounds exemplify anion sources and dihydrocarbyl-substituted bis(cyclopentadienyl) zirconium compounds exemplify the Group IV-B metal cation sources.

20 Claims, No Drawings

CATALYSTS, METHOD OF PREPARING THESE CATALYSTS, AND POLYMERIZATION PROCESSES WHEREIN THESE CATALYSTS ARE USED

This application is a continuation of application Ser. No. 08/123,400, filed Sept. 17, 1993, now abandoned, which is a divisional of application Ser. No. 07/875,165, filed Apr. 28, 1992, now issued as U.S. Pat. No. 5,278,119, which is a continuation of application Ser. No. 07/133,052, filed Dec. 21, 1987, now abandoned, which is a continuation-in-part of application Ser. No. 07/011,471, filed Jan.30, 1987, now abandoned.

BACKGROUND OF THE INVENTION

This invention relates to compositions of matter useful as catalysts, to a method for preparing these catalysts, to a process wherein these compositions of matter are used as catalysts and to polymeric products produced with these catalysts. More particularly, this invention relates to catalyst compositions, to a method of making said catalyst compositions, to a method for polymerizing olefins, diolefins and/or acetylenically unsaturated monomers wherein these catalyst compositions are used, and to polymeric products produced with these catalyst compositions.

The use of soluble Ziegler-Natta type catalysts in the polymerization of olefins is, of course, well known in the prior art. In general, these soluble systems comprise a Group IV-B metal compound and a metal alkyl cocatalyst, particularly an aluminum alkyl cocatalyst. A subgenus of these catalysts is that subgenus comprising a bis(cyclopentadienyl) compound of the Group IV-B metals, particularly titanium, and an aluminum alkyl cocatalyst. While speculation remains concerning the actual structure of the active catalyst species in this subgenus of soluble Ziegler-Natta type olefin polymerization catalysts, it would appear generally accepted that the active catalyst species is an ion or a decomposition product thereof which will alkylate an olefin in the presence of a labile stabilizing anion. This theory may have first been advocated by Breslow and Newburg, and Long and Breslow, as indicated in their respective articles appearing in J. Am. Chem. Soc., 1959, Vol. 81, pp. 81–86, and 0. Am. Chem. Soc., 1960, Vol. 82, pp. 1953–1957. As indicated in these articles, various studies suggested that the active catalyst species is a titanium-alkyl complex or a species derived therefrom when a titanium compound; viz., bis(cyclopentadienyl)titanium dihalide, and an aluminum alkyl are used as a catalyst or catalyst precursor. The presence of ions, all being in equilibrium, when a titanium compound is used was also suggested by Dyachkovskii, Vysokomol. Soyed., 1965,Vol. 7, pp. 114–115 and by Dyachkovskii, Shilova and Shilov, Polym. Sci., Part C, 1967, pp. 2333–2339. That the active catalyst species is a cation complex when a titanium compound is used, was further suggested by Eisch et al., 3. Am. Chem. Soc., 1985, Vol. 107, pp. 7219–7221.

While the foregoing articles teach or suggest that the active catalyst species is an ion pair and, particularly an ion pair wherein the metal component is present as a cation or a decomposition product thereof, and while these references teach or suggest coordination chemistry to form such active catalyst species, all of the articles teach the use of a cocatalyst comprising a Lewis acid either to form or to stabilize the active ionic catalyst species. The active catalyst is, apparently, formed through a Lewis acid-Lewis base reaction of two neutral components (the metallocene and the aluminum alkyl), leading to an equilibrium between a neutral, apparently inactive, adduct and an ion pair, presumably the active catalyst. As a result of this equilibrium, there is a competition for the anion which must be present to stabilize the active cation catalyst species. This equilibrium is, of course, reversible and such reversal will deactivate the catalyst. Moreover, the catalyst systems heretofore contemplated are subject to poisoning by the presence of basic impurities in the system. Further, many, if not all, of the Lewis acids heretofore contemplated for use in soluble Ziegler-Natta type catalyst systems are chain transfer agents and, as a result, prevent effective control of the product polymer molecular weight and product molecular weight distribution. Still further, most, if not all, of the cocatalysts heretofore contemplated are highly pyrophoric and, as a result, somewhat hazardous to use.

The aforementioned catalyst systems have not, generally, been particularly active when zirconium or hafnium is the Group IV-B metal used. Recently, however, it has been found that active Ziegler-Natta type catalysts can be formed when bis(nyl)cyclopentadienyl)hafnium and bis(cyclopentadienyl)zirconium compounds are used with alumoxanes. As is well known, these systems offer several distinct advantages, including vastly higher catalytic activities than the aforementioned bis (cyclopentadienyl)titanium catalysts and the production of polymers with narrower molecular weight distributions than those from conventional Ziegler-Natta catalysts. These systems remain subject to poisoning when basic impurities are present and do, however, require an undesirable excess of the alumoxane to function efficiently. Moreover, the hafnium containing systems are not as active as the zirconium containing systems, at least when used for homopolymerization. This has been suggested by Giannetti, Nicoletti, and Mazzocchi, J. Polym. Sci., Polym. Chem., 1985, Vol. 23, pp. 2117–2133, who claimed that the ethylene polymerization rates of bis(cyclopentadienyl)hafnium compounds were five to ten times slower than those of similar bis(cyclopentadienyl)zirconium compounds while there was little difference between the two catalysts in the molecular weight of the polyethylene formed from them.

In light of the several deficiencies of the coordination catalyst systems heretofore contemplated, the need for an improved coordination system which: (1) permits better control of molecular weight and molecular weight distribution; (2) is not subject to activation equilibrium; and (3) does not involve the use of an undesirable cocatalyst is believed readily apparent.

SUMMARY OF THE INVENTION

It has now been discovered that the foregoing and other disadvantages of the prior art ionic olefin polymerization catalysts can be avoided, or at least reduced, with the ionic catalysts of the present invention and an improved olefin, diolefin and/or acetylenically unsaturated monomer polymerization process provided therewith. It is, therefore, an object of this invention to provide improved ionic catalyst systems useful in the polymerization of olefins, diolefins and acetylenically unsaturated monomers. It is another object of this invention to provide a method for preparing such improved catalysts. It is a further object of this invention to provide an improved polymerization process using such improved catalysts. It is still another object of this invention to provide such an improved catalyst which is not subject to ion equilibrium reversal. It is still a further object of this invention to provide such an improved catalyst which may permit better control of the product polymer molecular weight and molecular weight distribution. It is yet a further object of this invention to provide such an improved catalyst which may be used with less risk of fire. It is even another object of this invention to provide polymeric products produced with these improved catalysts having relatively narrow molecular weight distributions and which are free of certain metal impurities. The foregoing and still other objects and advantages of the present invention will become apparent from the description set forth hereinafter and the examples included herein.

In accordance with the present invention, the foregoing and other objects and advantages are accomplished with and by using a catalyst prepared by combining at least two components, the first of which is a soluble, bis(cyclopentadienyl)-substituted Group IV-B metal compound containing at least one ligand which will combine with a Lewis or Bronsted acid thereby yielding a Group IV-B metal cation and the second of which compounds comprises a cation capable of donating a proton and reacting irreversibly with said ligand in said Group IV-B metal compound to liberate a free, neutral by-product and a compatible noncoordinating anion comprising a plurality of boron atoms, which compatible noncoordinating anion is stable, bulky and labeled The soluble Group IV-B metal compound must be capable of forming a cation formally having a coordination number of 3 and a valence of +4 when said ligand is liberated therefrom. The anion of the second compound must be capable of stabilizing the Group IV-B metal cation complex without interfering with the Group IV-B metal cation's or its decomposition product's ability to function as a catalyst and must be sufficiently labile to permit displacement by an olefin, a diolefin or an acetylenically unsaturated monomer during polymerization. For example, Bochmann and Wilson have reported (J. Chem. Soc., Chem. Comm., 1986, pp. 1610–1611) that bis(cyclopentadienyl)-titanium dimethyl reacts with tetrafluoroboric acid to form bis(cyclopentadienyl)titanium methyl tetrafluoroborate. The anion is, however, insufficiently labile to be displaced by ethylene.

DETAILED DESCRIPTION OF THE INVENTION

As indicated supra, the present invention relates to catalysts, to a method for preparing such catalysts, to a method of using such catalysts and to polymeric products produced with such catalysts. The catalysts are particularly useful in the polymerization of α-olefins, diolefins and acetylenically unsaturated monomers. The improved catalysts are prepared by combining at least one first compound which is a bis-(cyclopentadienyl) derivative of a metal of Group IV-B of the Periodic Table of the Elements capable of forming a cation formally having a coordination number of 3 and a valence of +4 and at least one second compound comprising a cation capable of donating a proton and a compatible noncoordinating anion comprising a plurality of boron atoms, which anion is both bulky and labile, and capable of stabilizing the Group IV-B metal cation without interfering with said Group IV-B metal cation's or its decomposition product's ability to polymerize α-olefins, diolefins and/or acetylenically unsaturated monomers.

All reference to the Periodic Table of the Elements herein shall refer to the Periodic Table of the Elements, as published and copyrighted by CRC Press, Inc., 1984. Also, any reference to a Group or Groups of such Periodic Table of the Elements shall be to the Group or Groups as reflected in this Periodic Table of the Elements.

As used herein, the recitation "compatible noncoordinating anion" means an anion which either does not coordinate to said cation or which is only weakly coordinated to said cation thereby remaining sufficiently labile to be displaced by a neutral Lewis base. The recitation "compatible noncoordinating anion" specifically refers to an anion which when functioning as a stabilizing anion in the catalyst system of this invention does not transfer an anionic substituent or fragment thereof to said cation thereby forming a neutral four coordinate metallocene and a neutral boron by-product. Compatible anions are those which are not degraded to neutrality when the initially formed complex decomposes.

The Group IV-B metal compounds, and particularly titanium, zirconium and hafnium compounds, useful as first compounds in the improved catalyst of this invention are bis(cyclopentadienyl) derivatives of titanium, zirconium and hafnium. In general, useful titanium, zirconium and hafnium compounds may be represented by the following general formulae:

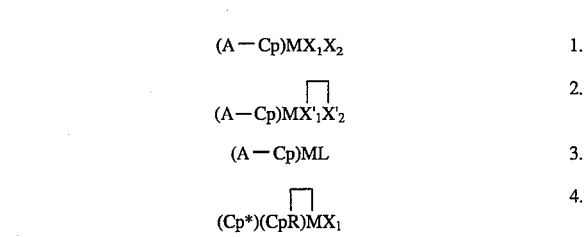

Wherein: M is a metal selected from the Group consisting of titanium (Ti), zirconium (Zr) and hafnium (Hf); (A-Cp) is either (Cp)(Cp$^*$) or Cp-A'-Cp$^*$ and Cp and Cp$^*$ are the same or different substituted or unsubstituted cyclopentadienyl radicals, wherein A' is a covalent bridging group containing a Group IV-A element; L is an olefin, diolefin or aryne ligand; $X_1$ and $X_2$ are, independently, selected from the Group consisting of hydride radicals, hydrocarbyl radicals having from 1 to about 20 carbon atoms, substituted-hydrocarbyl radicals, wherein 1 or more of the hydrogen atoms are replaced with a halogen atom, having from 1 to about 20 carbon atoms, organo-metalloid radicals comprising a Group IV-A element wherein each of the hydrocarbyl substituents contained in the organo portion of said organo-metalloid, independently, contain from 1 to about 20 carbon atoms and the like; $X'_1$ and $X'_2$ are joined and bound to the metal atom to form a metallacycle, in which the metal, $X'_1$ and $X'_2$ form a hydrocarbocyclic ring containing from about 3 to about 20 carbon atoms; and R is a substituent, preferably a hydrocarbyl substituent, having from 1 to about 20 carbon atoms, on one of the cyclopentadienyl radicals which is also bound to the metal atom.

Each carbon atom in the cyclopentadienyl radical may be, independently, unsubstituted or substituted with the same or a different radical selected from the Group consisting of hydrocarbyl radicals, substituted-hydrocarbyl radicals wherein one or more hydrogen atoms is replaced by a halogen atom, hydrocarbyl-substituted metalloid radicals wherein the metalloid Is selected from Group IV-A of the Periodic Table of the Elements, halogen radicals and the like. Suitable hydrocarbyl and substituted-hydrocarbyl radicals which may be substituted for at least one hydrogen atom In the cyclopentadienyl radical will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals. Similarly, and when $X_1$ and/or $X_2$ is a hydrocarbyl or substituted-hydrocarbyl radical, each may, independently, contain from 1 to about 20 carbon atoms and be a straight or branched alkyl radical, a cyclic hydrocarbyl radical, an alkyl-substituted cyclic hydrocarbyl radical, an aromatic radical or an alkyl-substituted aromatic radical. Suitable organo-metalloid radicals include mono-, di- and trisubstituted organo-metalloid radicals of Group IV-A elements wherein each of the hydrocarbyl Groups contains from 1 to about 20 carbon atoms. Suitable organo-metalloid radicals include trimethylsilyl, triethylsilyl, ethyldimethylsilyl, methyldiethylsilyl, triphenylgermyl, trimethylgermyl and the like.

Illustrative, but not limiting examples of bis(cyclopentadienyl)zirconium compounds which may be used in the preparation of the improved catalyst of this invention are dihydrocarbyl-substituted bis(cyclopentadienyl) zirconium compounds such as bis(cyclopentadienyl) zirconium dimethyl, bis(cyclopentadienyl)zirconium diethyl, bis(cyclopentadienyl) zirconium dipropyl, bis(cyclopentadienyl)zirconium dibutyl, bis(cyclopentadienyl)zirconium diphenyl, bis(cyclopentadienyl) zirconium dineopentyl, bis(cyclopentadienyl)zirconium di(m-tolyl), bis(cyclopentadienyl)zirconium di(p-tolyl) and the like; (monohydrocarbyl-substituted cyclopentadienyl)zirconium compounds such as (methylcyclopentadienyl)(cyclopentadienyl) and bis(methylcyclopentadienyl)zirconium dimethyl, (ethylcyclopentadienyl)(cyclopentadienyl) and bis(ethylcyclopentadienyl) zirconium dimethyl, (propylcyclopentadienyl)(cyclopentadienyl) and bis(propylcyclopentadienyl)zirconium dimethyl, (n-butyl cyclopentadienyl) (cyclopentadienyl) and bis(n-butylcyclopentadienyl) zirconium dimethyl, (t-butylcyclopentadienyl)(cyclopentadienyl) and bis(t-butylcyclopentadienyl)zirconium dimethyl, (cyclohexylmethylcyclopentadienyl)(cyclopentadienyl) and bis(cyclohexylmethylcyclopentadienyl) zirconium dimethyl, (benzyl cyclopentadienyl) (cyclopentadienyl) and bis-(benzylcyclopentadienyl)zirconium dimethyl, (diphenylmethylcyclopentadienyl)(cyclopentadienyl) and bis(diphenylmethylcyclopentadienyl zirconium dimethyl, (methylcyclopentadienyl)(cyclopentadienyl) and bis(methylcyclopentadienyl)zirconium dihydride, (ethylcyclopentadienyl) (cyclopentadienyl) and bis(ethylcyclopentadienyl)zirconium dihydride, (propylcyclopentadienyl)(cyclopentadienyl) and bis(propylcyclopentadienyl)zirconium dihydride, (n-butylcyclopentadienyl) (cyclopentadienyl) and bis(n-butylcyclopentadienyl) zirconium dihydride, (t-butylcyclopentadienyl)(cyclopentadienyl) and bis(t-butylcyclopentadienyl)zirconium dihydride, (cyclohexylmethylcyclopentadienyl)(cyclopentadienyl) and bis(cyclohexylmethylcyclopentadienyl)zirconium dihydride, (benzylcyclopentadienyl) (cyclopentadienyl) and bis(benzylcyclopentadienyl)zirconium dihydride, (diphenylmethylcyclopentadienyl) cyclopentadienyl) and bis(diphenylmethylcyclopentadienyl)zirconium dihydride and the like; (polyhydrocarbyl-substituted cyclopentadienyl)zirconium compounds such as (dimethylcyclopentadienyl)cyclopentadienyl) and bis(dtmethylcyclopentadienyl)zirconium dimethyl, (trimethylcyclopentadienyl) (cyclopentadienyl) and bis(trimethylcyclopentadienyl)zirconium dimethyl, (tetramethylcyclopentadienyl)(cyclopentadienyl) and bis(tetramethylcyclopentadienyl)zirconium dimethyl, (permethylcyclopentadienyl)(cyclopentadienyl) and bis(permethylcyclopentadienyl)zirconium dimethyl, (ethyltetramethylcyclopentadienyl)(cyclopentadienyl) and bis-(ethyltetramethylcyclopentadienyl) zirconium dimethyl, (indenyl)(cyclopentadienyl) and bis(indenyl) zirconium dimethyl, (dimethylcyclopentadienyl)(cyclopentadienyl) and bis(dimethylcyclopentadienyl)zirconium dihydride. (trimethylcyclopentadienyl)(cyclopentadienyl) and bis(trimethylcyclopentadienyl)zirconium dihydride, (tetramethylcyclopentadienyl) (cyclopentadienyl) and bis(tetramethylcyclopentadienyl)zirconium dihydride, (permethylcyclopentadienyl) (cyclopentadienyl ) and bis(permethylcyclopentadienyl)zirconium dthydride, (ethyltetramethylcyclopentadienyl)(cyclopentadienyl) and bis(ethyltetramethylcyclopentadieny)zirconium dihydride, (indenyl)(cyclopentadienyl) and bis(indenyl)zirconium dihydride and the like; (metal hydrocarbyl-substituted cyclopentadienyl)zirconium compounds such as (trimethylsilylcyclopentadienyl) (cyclopentadienyl) and bis(trimethylsilylcyclopentadienyl) zirconium dimethyl, (trimethylgermylcyclopentadienyl)(cyclopentadienyl) and bis(trimethylgermylcyclopentadienyl)zirconium dimethyl, (trimethylstannylcyclopentadienyl) (cyclopentadienyl) and bis(trimethylstannylcyclopentadienyl)zirconium dimethyl, (trimethylplumbylcyclopentadienyl)(cyclopentadienyl) and bis(trimethylplumbylcyclopentadienyl)zirconium dimethyl, (trimethylsilylcyclopentadienyl)(cyclopentadienyl) and bis(trimethylsilylcyclopentadienyl)zirconium dihydride, (trimethylgermylcyclopentadienyl)(cyclopentadienyl) and bis(trimethylgermylcyclopentadienyl)zirconium . dihydride, (trimethylstannylcyclopentadienyl)(cyclopentadienyl) and bis(trimethylstannylcyclopentadienyl)zirconium dihydride, (trimethylplumbylcyclopentadienyl)(cyclopentadienyl) and bis(trimethylplumbylcyclopentadienyl)zirconium dihydride and the like; (halogen-substituted-cyclopentadieneyl)zirconium compounds such as (trifluoromethylcyclopentadienyl)(cyclopentadienyl) and bis (trifluoromethylcyclopentadienylzirconium dimethyl. (trifluoromethyl cyclopentadienyl) (cyclopentadienyl) and bis(trifluoromethylcyclopentadienyl)zirconiumdihydride and the like; silyl-substituted bis(cyclopentadienyl)zirconium compounds such as bis(cyclopentadienyl)(trimethylsilyl)(methyl)zirconium, bis(cyclopentadienyl)(triphenylsilyl)(methyl)zirconium, bis(cyclopentadienyl)[tris(dimethylsilyl)silyl](methyl)zirconium, bis(cyclopentadienyl) [bis(mesityl)silyl](methyl)zirconium, bis(cyclopentadienyl)(trimethylsilyl)(trimethylsilylmethyl)zirconium, bis(cyclopentadienyl)(trimethylsilyl)(benzyl) and the like; (bridged-cyclopentadienyl)zirconium compounds such as methylene bis(cyclopentadienyl) zirconium dimethyl, ethylene bis(cyclopentadienyl)zirconium dimethyl, dimethylsilyl bis(cyclopentadienyl)zirconium dimethyl, methylene bis(cyclopentadtenyl)zirconium dihydride, ethylene bis(cyclopentadienyl)zirconium dihydride and dimethylsilyl bis(cyclopentadienyl)zirconium dihydride and the like; zirconacycles such as bis(pentamethylcyclopentadienyl) zirconalobutane, bis(pentamethyl cyclopentadienyl) zirconacyclopentane, bis(cyclopentadienyl)zirconaindane and the like; olefin, diolefin and aryne ligand substituted bis(cyclopentadlenyl)zirconium compounds such as bis(cyclopentadienyl) (1,3-butadiene)zirconium, bis(cyclopentadienyl) (2,3-dimethyl-1,3-butadiene)zirconium, bis(pentamethylcyclopentadienyl)(benzyne) zirconium and the like; (hydrocarbyl)(hydride) bis(cyclopentadienyl)zirconium) compounds such as bis(pentamethylcyclopentadienyl)zirconium (phenyl)(hydride), bis(pentamethyl cyclopentadienyl)zirconium (methyl)(hydride) and the like; and bis(cyclopentadienyl)zirconium compounds in which a substituent on the cyclopentadienyl radical is bound to the metal such as (pentamethyl cyclopentadienyl) (tetramethyl cyclopentadienylmethylene) zirconium hydride, (pentamethylcyclopentadienyl)(tetramethyl cyclopentadienylmethylene) zirconium phenyl and the like.

A similar list of illustrative bis(cyclopentadienyl) hafnium and bis(cyclopentadtenyl)titanium compounds could be made, but since the lists would be nearly identical to that already presented with respect to bis(cyclopentadienyl)zirconium compounds, such lists are not deemed essential to a complete disclosure. Those skilled in the art, however, are aware that bis(cyclopentadienyl)hafnium compounds and bis(cyclopentadtenyl) titanium compounds corresponding to certain of the bis(cyclopentadienyl) zirconium compounds listed supra are not known. The lists would, therefore, be reduced by these compounds. Other bis(cyclopentadienyl)hafnium compounds and other bis(cyclopentadienyl)titanium compounds as well as other bis(cyclopentadienyl)zirconium compounds which are useful in the catalyst compositions of this invention will, of course, be apparent to those skilled in the art.

Compounds useful as a second component in the preparation of the catalyst of this invention will comprise a cation, which is a Bronsted acid capable of donating a proton, and a compatible anion containing a plurality of boron atoms, which anion is relatively large, capable of stabilizing the active catalyst species which is formed when the two compounds are combined and said anion will be sufficiently labile to be displaced by olefinic, diolefinic and acetylenically unsaturated substrates or other neutral Lewis bases such as ethers. nitriles and the like. In general, a second compound useful in the preparation of the catalysts of this invention may be any compound represented by one of the following general formulae:

5. $[L'—H]C+[(CX)_a(BX')_mX''_b]^{c-}$

Wherein:

L'-H is either $H^+$, ammonium or a substituted ammonium cation having up to 3 hydrogen atoms replaced with a hydrocarbyl radical containing from 1 to about 20 carbon atoms or a substituted-hydrocarbyl radical, wherein one or more of the hydrogen atoms is replaced by a halogen atom, containing from 1 to about 20 carbon atoms, phosphonium radicals, substituted-phosphonium radicals having up to 3 hydrogen atoms replaced with a hydrocarbyl radical containing from 1 to about 20 carbon atoms or a substituted-hydrocarbyl radical, wherein 1 or more of the hydrogen atoms is replaced by a halogen atom, containing from 1 to about 20 carbon atoms and the like; B and C are, respectively, boron and carbon; X, X' and X" are radicals selected, independently, from the Group consisting of hydride radicals, halide radicals, hydrocarbyl radicals containing from 1 to about 20 carbon atoms, substituted-hydrocarbyl radicals, wherein one or more of the hydrogen atoms is replaced by a halogen atom, containing from 1 to about 20 carbon atoms, organo-metalloid radicals wherein each hydrocarbyl substitution in the organo portion contains from 1 to about 20 carbon atoms and said metal is selected from Group IV-A of the Periodic Table of the Elements and the like; a and b are integers>0; c is an integer>1; a+b+c=an even-numbered integer from 2 to about 8; and m is an integer ranging from 5 to about 22.

6. $[L'-H]C^+[[[(CX_3)_a(BX_4)_m(X_5)_b]^{c-}]_2M^{n+}]^{d-}$

Wherein: L'-H is either $H^+$ ammonium or a substituted ammonium radical having up to 3 hydrogen atoms replaced with a hydrocarbyl radical containing from 1 to about 20 carbon atoms or a substituted-hydrocarbyl radical, wherein 1 or more of the hydrogen atoms is replaced by a halogen atom, containing from 1 to about 20 carbon atoms, a phosphonium radical, a substituted-phosphonium radical having up to 3 hydrogen atoms replaced with a hydrocarbyl radical containing from 1 to about 20 carbon atoms or a substituted-hydrocarbyl radical, wherein 1 or more of the hydrogen atoms is replaced by a halogen atom, containing from 1 to about 20 carbon atoms and the like; B, C, M and H are, respectively, boron; carbon, a transition metal and hydrogen; $X_3$, $X_4$, and $X_5$ are radicals selected, independently, from the Group consisting of hydride radicals, halide radicals, hydrocarbyl radicals containing from 1 to about 20 carbon atoms, substituted-hydrocarbyl radicals, wherein one or more of the hydrogen atoms is replaced by a halogen atom, containing from 1 to about 20 carbon atoms, organo-metalloid radicals wherein each hydrocarbyl substitution in the organo portion or said organo-metalloid contains from 1 to about 20 carbon atoms and said metal is selected from Group IV-A of the Periodic Table of the Elements and the like; a' and b' are the same or a different integer>0; c' is an integer>2; a'+b'+c'=an even-numbered integer from 4 to about 8; m' is an integer from 6 to about 12; n is an integer such that 2c'–n=d; and d is an integer>1.

Illustrative, but not limiting, examples of the second compounds which can be used as a second component in the catalyst compositions of this invention are ammonium salts such as ammonium 1-carbadodecaborate (using 1-carbadodecaborate as an illustrative, but not limiting, counterion for the ammonium cations listed below): monohydrocarbyl-substituted ammonium salts such as methylammonium 1-carbadodecaborate, ethylammonium 1-carbadode-cabo-rate, propylammonium 1-carbadodecaborate, isopropylammonium 1-carbadodecaborate, (n-butyl)ammonium 1-carbadodecaborate, anilinium 1-carbadodecaborate, and (p-tolyl)ammonium 1-carbadodecaborate and the like; dihydrocarbyl-substituted ammonium salts such as dimethylammonium 1-carbadodecaborate, diethylammonium 1-carbadodecaborate, dipropylammonium 1-carbadodecaborate, diisopropylammonium 1-carbadodecaborate, di(n-butyl)ammonium 1-carbadodecaborate, diphenylammonium 1-carbadodecaborate, di(p-tolyl)ammonium 1-carbadodecaborate and the like; trihydrocarbyl-substituted ammonium salts such as trimethylammonium 1-carbadodecaborate, triethylammonium 1-carbadodecaborate, tripropylammonium 1-carbadodecaborate, tri(n-butyl) ammonium 1-carbadodecaborate, triphenylammonium 1-carbadodecaborate, tri(p-tolyl)ammonium 1-carbadodecaborate, N,N-dimethylanilinium 1-carbadodecaborate, N,N-diethylanilinium 1-carbadodecaborate and the like Illustrative, but not limiting examples of second compounds corresponding to Formula 5 [using tri(n-butyl) ammonium as an illustrative, but not limiting, counterion for the anions listed below are salts of anions such as bis[tri(n-butyl)ammonium] nonaborate, bis[tri(n-butyl)ammonium] decaborate, bis [tri(n-butyl)ammonium]undecaborate, bis [tri(n-butyl)ammonium] dodecaborate, bis[tri(n-butyl)ammonium]decachlorodecaborate, bis[tri(n-butyl)ammonium]dodecachlorododecaborate, tri(n-butyl)ammonium 1-carbadecaborate, tri(n-butyl)ammonium 1-carbaundecaborate, tri(n-butyl)ammonium 1-carbadodecaborate, tri(n-butyl)ammonium 1-trimethylsilyl-1-carbadecaborate, tri(n-butyl)ammonium dibromo-1-carbadodecaborate and the like; borane and carborane complexes and salts of borane and carborane anions such as decaborane(14), 7,8-dicarbaundecaborane(13), 2,7-dicarbaundecaborane)(13), undecahydrido-7,8-dimethyl-7,8-dicarbaundecaborane, dodecahydrido-11-methyl-2,7-dicarbaundecaborane, tri(n-butyl)ammonium undecaborate(14), tri(n- butyl)ammonium 6-carbadecaborate(12), tri(n-butyl)ammonium 7-carbaundecaborate(13), tri(n-butyl)ammonium 7,8-dicarbaundecaborate(12), tri(n-butyl)ammonium 2,9-dicarbaundecaborate(12), tri(n-butyl)ammonium dodecahydrido-8-methyl-7,9-dicarbaundecaborate, tri(n-butyl)ammonium undecahydrido-8-ethyl-7,9-dicarbaundecaborate, tri(n-butyl)ammonium undecahydrido-8-butyl-7,9-dicarbaundecaborate, tri(n-butyl)ammonium undecahydrido-8-allyl-7,9-dicarbaundecaborate, tri(n-butyl)ammonium undecahydrido-9-trimethylsilyl-7,8-dicarbaundecaborate, tri(n-butyl)ammonium undecahydrido-4,6-dibromo-7-carbaundecaborate and the like; boranes and carboranes and salts of boranes and carboranes such as 4-carbanonaborane(14),1,3-dicarbanonaborane(13), 6,9-dicarbadecaborane(14), dodecahydrido-1-phenyl-1,3-dicarbanonaborane, dodecahydrido-1-methyl-1,3dicarbanonaborane, undecahydrido-1,3-dimethyl-1,3-dicarbanonaborane and the like.

Illustrative, but not limiting, examples of second compounds corresponding to Formula 6 [using tri(n-butyl)ammonium as an illustrative, but not limiting, counterion for the anions listed below] are salts of metallacarborane and metallaborane anions such as tri(n-butyl) ammonium bis(nonahydrido-1,3-dicarbanonaborato) cobaltate(III), tri(n-butyl)ammonium bis(nondecahydrido-7,8dicarbanonaborato)ferrate) (III), tri(n-butyl)ammonium bis(undecahydrido-7,8,-dicarbaundecaborato)cobaltate(III), tri(n-butyl) ammonium bis(undecahydrido-7,8-dicarbaundecaborato) nickelate(III), tri(n-butyl)ammonium bis(undecahydrido-7,8-dicarbaundecaborato) cuprate(III), tri(n-butyl)ammonium bis(undecahydrido-7,8-dicarbaundecaborato)aurate(III), tri(n-butyl)ammonium bis(nonahydrido7,8-dimethyl-7,8-dicarbaundecaborato)-ferrate(III), tri(n-butyl) ammonium bis(nonahydrido-7,8-dimethyl-7,8-dicarbaundecaborato) chromate(III), tri(n-butyl)ammonium bis(tribromooctahydrido7,8-dicarbaundecaborato)cobaltate(III), tri(n-butyl) ammonium bis(dodecahydridodicarbadodecaborato)cobaltate(III), bis[tri(n-butyl)ammonium] bis(dodecahydridodecaborato) nickelate(II), tris[tri(n-butyl)ammonium] bis(undecahydrido-7carbaundecaborato) chromate(III), bis[tri(n-butyl) ammonium] bis(undecahydrido-7-carbaundecaborato)manganate(IV), bis[tri(n-butyl)ammonium] bis(undecahydrido-7-carbaundecaborato) cobaltate(III), bis[tri(n-butyl)ammonium] bis(undecahydrido-7-carbaundecaborato)nickelate(IV) and the like. A similar list of representative phosphonium compounds could be recited as illustrative second compounds, but for the sake of brevity, it is simply noted that the phosphonium and substituted-phosphonium salts corresponding to the listed ammonium and substituted-ammonium salts could be used as second compounds in the present invention.

In general, and while most first components identified above may be combined with most second components identified above to produce an active olefin polymerization catalyst, it is important to continued polymerization operations that either the initially formed metal cation or a decomposition product thereof be a relatively stable olefin polymerization catalyst. It is also important that the anion of the second compound be stable to hydrolysis when an ammonium salt is used. Further, it is important that the acidity of the second component be sufficient, relative to the first, to facilitate the needed proton transfer. Conversely, the basicity of the metal complex must also be sufficient to facilitate the needed proton transfer. Certain metallocene compounds—using bis(pentamethylcyclopentadienyl (hafnium dimethyl as an illustrative, but not limiting, example—are resistant to reaction with all but the strongest Bronsted acids and thus are not suitable as first components to form the catalysts described herein. In general, bis(cyclopentadienyl)metal compounds which can be hydrolyzed by aqueous solutions can be considered suitable as first components to form the catalysts described herein.

With respect to the combination of the desired cation and the stabilizing anion to form an active catalyst of the present invention, it should be noted that the two compounds combined for preparation of the active catalyst must be selected so as to ensure displacement of the anion by monomer or another neutral Lewis base. This could be done by steric hindrance, resulting from substitutions on the cyclopentadienyl carbon atoms as well as from substitutions on the anion itself. The use of perhydrocarbyl-substituted cyclopentadienyl metal compounds and/or bulky second components does not generally prevent the desired combination and, in fact, generally yields more labile anions. It follows, then, that metal compounds (first components) comprising perhydrocarbylsubstituted cyclopentadienyl radicals could be effectively used with a wider range of second compounds than could metal compounds (first components) comprising unsubstituted cyclopentadienyl radicals. In fact, first compounds comprising perhydrocarbyl-substituted cyclopentadtenyl radicals would, generally, be effective when used in combination with second components having both larger and smaller anions. As the amount and size of the substitutions on the cyclopentadienyl radicals are reduced, however, more effective catalysts are obtained with second compounds containing larger anions, such as those encompassed by Equation 6 above and those having larger m values in Equation 5. In these cases, it is further preferable that in using second compounds which are encompassed by Equation 5, a+b+c=2. Second compounds in which a+b+c= even-numbered integers of 4 or more have acidic B-H-B moieties which can react further with the metal cation formed, leading to catalytically inactive compounds.

In general, the catalyst can be prepared by combining the two components in a suitable solvent at a temperature within the range from about −100° C. to about 300° C. The catalyst may be used to polymerize α-olefins and acetylenically unsaturated monomers having from two to about eighteen carbon atoms and diolefins having from four to about eighteen carbon atoms either alone or in combination. The catalyst may also be used to polymerize α-olefins, diolefins and/or acetylenically unsaturated monomers in combination with other unsaturated monomers. In general, the polymerization will be accomplished at conditions well known in the prior art for the polymerization of toohomers of this type. It will, of course, be appreciated that the catalyst system will form in situ if the components thereof are added directly to the polymerization process and a suitable solvent or diluent is used in said polymerization process. It is, however, preferred, to form the catalyst in a separate step prior to adding the same to the polymerization step. While the catalysts do not contain pyrophoric species, the catalyst components are sensitive to both moisture and oxygen and should be handled and transferred in an inert atmosphere such as nitrogen, argon or helium.

As indicated supra, the improved catalyst of the present invention will, generally, be prepared in a suitable solvent or diluent. Suitable solvents or diluents include any of the solvents known in the prior art to be useful as solvents in the polymerization of olefins. Suitable solvents, then, include, but are not necessarily limited to, straight and branched-chain hydrocarbons such as isobutane, butane, pentane, hexane, heptane, octane and the like, cyclic and allcyclic hydrocarbons such as cyclohexane, cycloheptane, methylcyclohexane, methylcycloheptane and the like and aromatic and alkyl substituted aromatic compounds such as benzene, toluene, xylene and the like. Suitable solvents also include basic solvents not heretofore useful as polymerization solvents when conventional Ziegler-Natta type polymerization catalysts are used such as chlorobenzene, dichloromethane and propyl chloride.

While the inventors do not wish to be bound by any particular theory, it is believed that when the two compounds used to prepare the improved catalysts of the present invention are combined in a suitable solvent or diluent, all or a part of the cation of the second compound (the proton) combines with one of the substituents on the metal-containing (first) component. In the case where the first component has a formula corresponding to that of general formula 1 supra, a neutral compound is liberated which either remains in solution or is liberated as a gas. In this regard, it should be noted that if the cation of the second compound is a proton and either $X_1$ or $X_2$ in the metal containing (first) compound is a hydride, hydrogen gas may be liberated. Similarly, if the cation of the second compound is a proton and either $X_1$ or $X_2$ is a methyl radical, methane may be liberated as a gas. In the cases where the first component has a formula corresponding to those of general formulae 2, 3 or 4, one of the substituents on the metal-containing (first) component is protonated but, in general, no substituent is liberated from the metal. It is preferred that the ratio of metal containing (first) component to second component cations be about 1:1 or greater. The conjugate base of the cation of the second compound, if such a portion does remain, will be a neutral compound which will remain in solution or complex with the metal cation formed, though, in general, a cation is chosen such that any binding of the neutral conjugate base to the metal cation will be weak or nonexistent. Thus, as the steric bulk of this conjugate base increases, it will, simply, remain in solution without interfering with the active catalyst. For example, if the cation of the second compound is an ammonium ion, this ion will liberate a hydrogen atom which may then react as in the case when the hydrogen atom was the cation to form gaseous hydrogen, methane or the like and the conjugate base of the cation will be ammonia. In like fashion, if the cation of the second compound were a hydrocarbyl-substituted ammonium ion containing at least one hydrogen atom, as is essential to the present invention, the hydrogen atom would be given up to react in the same fashion as when hydrogen were the cation and the conjugate base of the cation would be an amine. Further, if the cation of the second compound were a hydrocarbyl-substituted phosphonium ion containing at least one proton, as is essential to the present invention, the conjugate base of the cation would be phosphine.

While still not wishing to be bound by any particular theory, it is also believed that when the metal containing (first) component has reacted with the second component, the noncoordinating anion originally contained in the second compound used in the catalyst preparation combines with and stabilizes either the metal cation, formally having a coordination number of 3 and a +4 valence, or a decomposition product thereof. The cation and anion will remain so combined until the catalyst is contacted with one or more olefins. diolefins and/or acetylenically unsaturated monomers either alone or in combination with one or more other monomers. As indicated supra, the anion contained in the second compound must be sufficiently labtle to permit rapid displacement by an olefin, a diolefin or an acetylenically unsaturated monomer to facilitate polymerization.

As indicated supra, most first compounds identified above will combine with most second compounds identified above to produce an active catalyst, particularly an active polymerization catalyst. The actual active catalyst species is not, however, always sufficiently stable as to permit its separation and subsequent identification. Moreover, and while many of the initial metal cations are relatively stable, it has become apparent that the initially formed metal cation may decompose yielding either an active polymerization catalyst species or a catalytically inactive species. Most decomposition products are, however, catalytically active. While the inventors still do not wish to be bound by any particular theory, it is believed that the active catalyst species which have not been isolated, including active decomposition products, are of the same type as those which have been isolated and fully characterized or at least retain the essential structure required for functioning as a catalyst such as a reactive metal-carbon bond.

While still not wishing to be bound by any particular theory and as indicated supra, it is also believed that the extent and nature of the substitution on the cyclopentadienyl ring dictates the size of the stabilizing anion needed to generate a particularly active olefin polymerization catalyst. In this regard, it is believed that as the number of substituents on the cyclopentadienyl radical in the metallocene cation are decreased from 5 to 0, a given anion will become increasingly less labile. Thus, it is suggested that as the number of substituents on the cyclopentadienyl radical in the metallocene cation are reduced from 5 to 0, larger or less reactive anions should be used to ensure liability and allow for the generation of a particularly active catalyst species.

Consistent with the foregoing, stable, isolable, characterizible olefin polymerization catalysts have been prepared when bis(permethylcyclopentadienyl)zirconium dimethyl has been combined with and reacted with tri(n-butyl)ammonium 7,8-dicarbaundecaborate(12) or 7,8-dicarbaundecaborane(13). A stable, isolable, olefin polymerization catalyst has also been prepared when bis(ethyl tetramethyl cyclopentadienyl)zirconium dimethyl has been combined with 7,8-dicarbaundecaborane(13). In each of these cases, the stable polymerization catalyst was prepared by adding the reactants into a suitable solvent or diluent at a temperature within the range from about −100° C. to about 300° C. Based on this and other information available to the inventors, it appears clear that isolable and characterizable polymerization catalysts can also be prepared when a bis(perhydrocarbyl-substituted cyclopentadienyl)metal compound is combined with any one or more of the second compounds identified above. Also, active, but unisolated polymerization catalysts are prepared when bis(cyclopentadienyl )zirconium compounds containing less than five hydrocarbyl-substitutions on each cyclopentadienyl radical are reacted with a suitable second compound within the scope of the present invention, containing a cation capable of donating a proton and an anton capable of stabilizing the metallocene cation and sufficiently labile to be displaced by an olefin, a diolefin or an acetylenically unsaturated monomer during polymerization, particularly those second compounds having the larger anions.

The chemical reactions which occur may be represented by reference to the general formulae set forth herein as follows:

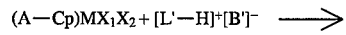 A.

-continued $[(A-Cp)MX_1]^+[B']^- + HX_2 + L'$ or $[(A-Cp)MX_2]^+[B']^- + HX_1 + L'$

B.

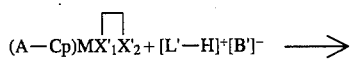

$\longrightarrow$

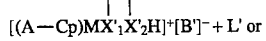 or

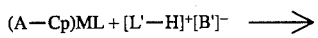 $\longrightarrow$  C.

$[(A-Cp)M(LH)]^+[B']^- + L'$

D.

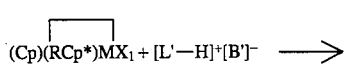 $\longrightarrow$

 + L' or

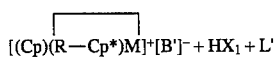

In the foregoing reaction equations, the letters A-D correspond to the numbers 1-4, respectively, set forth in combination with the general equations for useful metal locene compounds. B' represents a compatible ion corresponding to the general formulae outlined in formulae 5 and 6 above. The reaction of each of the four classes of metallocenes with N,N-dimethylaninium bis(7,8-dicarbaundecaborato)cobaltate(III) has been examined by solution $^1$H NMR or $^{13}$C NMR spectroscopy. In each case, products conforming to those outlined above were observed.

In general, the stable, isolable catalysts formed by the method of this invention may be separated from the solvent and stored for subsequent use. The unisolated catalysts, however, will, generally, be retained in solution until ultimately used in the polymerization of olefins. Alternatively, any of the catalysts prepared by the method of this invention may be retained in solution for subsequent use or used directly after preparation as a polymerization catalyst. Moreover, and as indicated supra, the catalysts may be prepared in situ by passing the separate components into the polymerization vessel where the components will be contacted and react to produce the improved catalyst of this invention.

In general, and as indicated supra, the improved catalyst of this invention will polymerize olefins, diolefins and/or acetylenically unsaturated monomers either alone or in combination with other olefins and/or other unsaturated monomers at conditions well known in the prior art for conventional Ziegler-Natta catalysis. In the polymerization process of this invention, the molecular weight appears to be a function of both catalyst concentration, polymerization temperature and polymerization pressure. In general, the polymers produced with the catalyst of this invention, when produced in an atmosphere free of hydrogen or other chain terminating agents, will contain terminal unsaturation.

The polymer products produced with the catalyst of this invention will, of course, be free of certain trace metals generally found in polymers produced with Ziegler-Natta type catalysts such as aluminum, magnesium, chloride and the like. The polymer products produced with the catalysts of this invention should then have a broader range of applications than polymers produced with more conventional Ziegler-Natta type catalysts comprising a metal alkyl, such as an aluminum alkyl.

PREFERRED EMBODIMENT OF THE INVENTION

In a preferred embodiment of the present invention, a polymerization catalyst will be prepared by combining a bis(cyclopentadienyl) compound of one of the Group IV-B metals, most preferably a bis(cyclopentadienyl)zirconium or bis(cyclopentadienyl)hafnium compound, containing two independently substituted or unsubstituted cyclopentadienyl radicals and two lower alkyl substituents or two hydrides with one of the following:

(1). A trisubstituted ammonium salt of a borane or carborane anion satisfying the general formula:

7. $[(CH)_{ax}(BH)_{bx}]^{cx-}$

Wherein:

B, C, and H are, respectively, boron, carbon and hydrogen; axis either 0 or 1; cx is either 1 or 2; ax+cx=2; and bx is an integer ranging from 10 to 12.

(2). A trisubstituted ammonium salt of a borane or carborane anion or a neutral borane or carborane compound satisfying the general formula:

8. $[(CH)_{ay}(BH)_{my}H_{by}]^{cy-}$

Wherein:

B, C and H are, respectively, boron, carbon and hydrogen; ay is an integer from 0 to 2; by is an integer from 0 to 3; cy is an integer from 0 to 3; ay+by+cy=4; and my is an integer from 9 to 18.

(3). A trisubstituted ammonium salt of a metallaborane or metallacarborane anion satisfying the general formula:

9. $[[[(CH)_{az}(BH)_{mz}H_{bz}]^{cz-}]_2 MZ^{nz+}]^{dz-}$

Wherein:

B, C, H and MZ are, respectively, boron, carbon, hydrogen and a transition metal; az is an integer from 0 to 2; bz is an integer from 0 to 2; cz is either 2 or 3; mz is an integer from 9 to 11; az+bz+cz=4; and nz and dz are, respectively, 2 & 2 or 3 & 1.

Each of the trisubstitutions in the ammonium cation will be the same or a different lower alkyl or aryl radical. By lower alkyl is meant an alkyl radical containing from one to four carbon atoms. In a most preferred embodiment of the present invention wherein an anton represented by Formula 7 is used, bis(pentamethylcyclopentadienyl)zirconium dimethyl will be combined with tri(n-butyl)ammonium 1-carbaundecaborate to produce a most preferred catalyst. In a most preferred embodiment of the present invention wherein an anton represented by Formula 8 is used, bis(pentamethyl cyclopentadi enyl )zirconium dimethyl will be combined with 7,8-dicarbaundecaborane(13) to produce a most preferred catalyst. In a most preferred embodiment of the present invention wherein an anion represented by Formula 9 is used, bis(cyclopentadienyl)zirconium or -hafnium dimethyl will be combined with N,N-dimethylaninium bis(7,8-dicarbaundecaborato) cobaltate(III) to produce a most preferred catalyst. In a preferred embodiment of this invention, the two components used to prepare the catalyst will be combined at a temperature within the range from about 0° C. to about 100° C. The components will be combined, preferably, in an aromatic hydrocarbon solvent, most preferably toluene. Nominal holding times within the range from about 10 seconds to about 60 minutes will be sufficient to produce both the preferred and most preferred catalysts of this invention.

In a preferred and most preferred embodiment of this invention, the catalyst, immediately after formation, will be used to polymerize one or more lower α-olefins, particularly ethylene and propylene, most preferably ethylene, at a temperature within the range from about 0° C. to about 100° C. and at a pressure within the range from about 15 to about 500 psig. The monomers will be maintained at polymerization conditions for a nominal holding time within the range from about 1 to about 60 minutes and the catalyst will be used at a concentration within the range of about $10^{-5}$ to about $10^{-1}$ moles per liter of solvent or diluent.

Having thus broadly described the present invention and a preferred and most preferred embodiment thereof, it is believed that the same will become even more apparent by reference to the following examples. It will be appreciated, however, that the examples are presented solely for purposes of illustration and should not be construed as limiting the invention. In the examples wherein an active catalyst was isolated and identified, the analysis was by solid-state $^{13}C$ NMR spectroscopy and solution $^{1}H$ NMR spectroscopy.

EXAMPLE 1

In this example, an active olefin polymerization catalyst was prepared and isolated by combining 1.0 g of bis(pentamethylcyclopentadienyl)zirconium dimethyl in 50 ml toluene and then adding 0.82 g of tri(n-butyl)ammonium 7,8-dicarbaundecaborate(12). The mixture was stirred at room temperature for 30 minutes, the solvent was evaporated to half its original volume and pentane added to the point of cloudiness. After cooling at −20° C. overnight, a yellow solid was filtered off, washed with pentane and dried. The yield of active catalyst was 0.75 g. A portion of this product was analyzed and identified as bis(pentamethylcyclopentadienyl)methyl (dodecahydrido-7,8-dicarbaundecaborato)zirconium.

EXAMPLE 2

In this example, an active olefin polymerization catalyst was prepared by dissolving 1.2 g of bis(pentamethylcyclopentadienyl)zirconium dimethyl in 100 ml pentane and then adding dropwise 5 ml of a toluene solution containing 0.38 g of 7,8-dicarbaundecaborane(13). A bright yellow solid precipitated from solution. After thirty minutes, the solid was filtered off, washed with pentane and dried. The yield of product was 0.95 g. A portion of the product was analyzed and identified as bis(pentamethylcyclopentadienyl)methyl (dodecahydrido-7,8-dicarbaundecaborato) zirconium, the same active catalyst produced in Example 1.

EXAMPLE 3

In this example, an active olefin polymerization catalyst was prepared by dissolving 0.425 g of bis(ethyltetramethylcyclopentadienyl)zirconium dimethyl in 60 ml of pentane and adding dropwise 5 ml of a toluene solution containing 0.125 g of 7,8-dicarbaundecaborane(13). A bright yellow solid precipitated from solution. After fifteen minutes, the solid was filtered off, washed with pentane and dried. The yield of product was 0.502 g. A portion of the product was analyzed and identified as bis(ethyltetramethyl cyclopentadienyl)methyl(dodecahydrido-7,8-di-carbaundecaborato)zirconium.

EXAMPLE 4

In this example, ethylene was polymerized using a portion of the catalyst produced in Example 2 by dissolving 50 mg of the catalyst in 100 ml of toluene and transferring the catalyst solution under a nitrogen atmosphere into a stirred, steel 1 liter autoclave which was previously flushed with nitrogen. The autoclave was pressured with 300 psig ethylene and stirred at 60° C. After thirty minutes, the reactor was vented and opened. The yield of linear polyethylene formed was 22.95 g.

EXAMPLE 5

In this example, ethylene was polymerized with the catalyst produced in Example 3 by dissolving 50 mg of the catalyst in 100 ml of toluene and transferring the catalyst solution under a nitrogen atmosphere into a stirred, steel 1 liter autoclave which was previously flushed with nitrogen. The autoclave was pressured with 400 psig ethylene and stirred at 40° C. After one hour, the reactor was vented and opened. The yield of linear polyethylene formed was 74.6 g.

EXAMPLE 6

In this example, ethylene was again polymerized with a portion of the catalyst produced in Example 2 by dissolving 75 mg of the catalyst in 100 ml of chlorobenzene and transferring under a nitrogen atmosphere into a stirred, steel 1 liter autoclave which was previously flushed with nitrogen. The autoclave was pressured with 150 psig ethylene and stirred at 40° C. After twenty minutes, the reactor was vented and opened. The field of linear polyethylene formed was 3.3 g.

EXAMPLE 7

In this example, ethylene was polymerized with an active catalyst formed in situ by dissolving 80 mg of bis(pentamethylcyclopentadienyl)zirconium dimethyl and 35 mg of 1,2-dicarbaundecaborane(13) in 20 ml of dichloromethane. Ethylene was then bubbled through the solution at atmospheric conditions for one minute and the slurry then poured into an excess of ethanol. The polyethylene formed was filtered off, washed with water and acetone and dried. The yield of polyethylene was 1.6 g.

EXAMPLE 8

In this example, an active catalyst was prepared by reacting bis(pentamethylcyclopentadienyl)zirconium dimethyl (46 mg) with octadecaborane(22) (20 mg) in toluene (5 ml). There was considerable gas evolution. On passing ethylene through the solution for one minute, the solution grew hot. The vial was opened and acetone added to precipitate the polymer, which was filtered off, washed with acetone, and dried. The yield of polymer isolated was 0.32 g.

EXAMPLE 9

In this example, an active catalyst was prepared by reacting bis(pentamethylcyclopentadienyl)zirconium dimethyl (40 mg) with tri(n-butyl)ammonium tridecahydrido-7-carbaundecaborate (30 mg) in toluene (50 ml) in a serum-capped round-bottomed flask. The solution turned from colorless to orange-yellow. On passing ethylene through the solution for 1 minute, the solution grew hot as polymer precipitated from solution.

EXAMPLE 10

In this example, an active catalyst was prepared in an NMR tube by combining 50 mg of bis(pentamethylcyclopentadienyl) zirconium dimethyl and 40 mg of tri(n-butyl)ammonium 1-carbadodecaborate in 1 ml of hexadeuteriobenzene and placing the solution into the NMR tube. The disappearance of starting material was then observed by $^1$H NMR spectroscopy and when the starting materials had disappeared ethylene was injected into the NMR tube. Solid polymer precipitated from the solution.

EXAMPLE 11

In this example, an active catalyst was again prepared in an NMR tube by dissolving 100 mg of bis[1,3-bis<trimethylsilyl) cyclopentadienyl]zirconium dimethyl and 60 mg of tri(n-butyl) ammonium 1-carbadodecarborate in 1 ml of hexadeuteriobenzene and then placing the solution into the NMR tube. The disappearance of starting materials was observed in the $^1$H NMR spectrum. When all of the starting zirconium compound had disappeared, ethylene was injected into the tube and solid polymer precipitated from solution.

EXAMPLE 12

In this example, an active catalyst was again formed in an NMR tube by dissolving 100 mg of (pentamethylcyclopentadienyl) [1,3-bis(trimethylsilyl)cyclopentadienyl]zirconium dimethyl and 70 mg of tri(n-butyl)ammonium 1-carbadodecaborate in 1 ml of hexadeuteriobenzene and then placing the solution in the NMR tube. Disappearance of starting material was followed by $^1$H NMR spectrum and when all of the starting zirconium compound had disappeared ethylene was injected into the tube. Solid ethylene polymer then precipitated from solution.

EXAMPLE 13

In this example, an active catalyst was prepared by suspending 80 mg bis (pentamethyl cyclopentadienyl)zirconium dimethyl and 50 mg of bis[tri(n-butyl)ammonium] dodecaborate in 7 ml of toluene in a serum capped vial. On mixing, the suspension turned from colorless to yellow-green. Bubbling ethylene through the solution for 30 seconds caused a white polymer to form as the solution became warm. The vial was opened and the polymer precipitated with ethanol. The yield of polyethylene was 0.13 g.

EXAMPLE 14

In this example, an active catalyst was prepared by reacting bis(pentamethylcyclopentadienyl)zirconium dimethyl (45 mg) with tri(n-butyl)ammonium undecahydrido-1-carbaundecaborate (30 mg) in toluene (5 ml) in a serum-capped vial. The solution turned from colorless to yellow. On passing ethylene through the solution for 30 seconds, the solution grew hot as polymer precipitated.

EXAMPLE 15

In this example, an active catalyst was prepared by suspending 80 mg of bis (pentamethyl cyclopentadienyl)zirconium dimethyl and 90 mg of N,N-dimethylanilinium bis(7,8-dicarbaundecaborato)cobaltate(III) in 5 ml of toluene in a serum-capped vial. The yellow solution turned orange-violet with gas evolution. On passing ethylene through the solution for 30 seconds, the solution turned deep violet with considerable evolution of heat and became viscous. The vial was opened and the solids precipitated with ethanol. These were washed with 10% aqueous sodium hydroxide solution, ethanol, acetone and hexane. The yield of polyethylene was 0.41 g.

EXAMPLE 16

In this example, an active catalyst was prepared by reacting bis(pentamethylcyclopentadienyl )zirconium dimethyl (40 mg) with N,N-dimethylanilinium bis(7,8-dicarbaundecaborato)ferrate(III) (45 mg) in toluene (10 ml) in a serum-capped vial. On passing ethylene through the solution, the mixture grew hot as polymer formed. The vial was opened and the contents diluted with acetone, then filtered and dried. The yield of polymer isolated was 0.33 g.

EXAMPLE 17

In this example, an active catalyst was prepared by reacting bis(pentamethylcyclopentadienyl )zirconium dimethyl (40 mg) with tri(n-butyl)ammonium bis(7,8-dicarbaundecaborato)nickelate (III) (45 mg) in toluene (30 ml) in a serum-capped round-bottomed flask. Ethylene was passed through the solution for one minute. The solution grew hot as polymer precipitated from solution. The flask was opened and the contents diluted with acetone. The solid polymer was filtered off, washed with acetone, and dried. The yield of isolated polymer was 0.48 g.

EXAMPLE 18

In this example, an active catalyst was prepared by suspending 100 mg of bis(methylcyclopentadienyl)zirconium dihydride and 180 mg of N,N-dimethylanilinium bis(7,8-dicarbaundecaborato) cobaltate(III) In 100 ml of toluene in a 250 ml round bottomed flask capped with a rubber septum. Ethylene was bubbled through the solution for 10 minutes. The flask was opened, the contents poured into hexane, filtered off and dried. The yield of polymer was 2.98 g.

EXAMPLE 19

In this example, an active catalyst was prepared by suspending 105 mg of bis[1,3-bis(trimethylsilyl)cyclopentadienyl[zirconium dimethyl and 90 mg of N,N-dimethylanilinium bis(7,8-dicarbaundecaborato)cobaltate(III) in 50 ml of toluene in a 100 ml round bottomed flask capped with a rubber septum. Ethylene was bubbled through the solution for 10 minutes. The flask was opened and the contents poured into ethanol and evaporated. The yield of polymer was 2.7 g.

EXAMPLE 20

In this example, an active catalyst was prepared by stirring 50 mg of bis(cyclopentadienyl)zirconium dimethyl and 90 mg of N,N-dimethylanilinium bis(7,8-dicarbaundecaborato)cobaltate(III) in 50 ml of toluene in a 100 ml round bottomed flask capped with a rubber septum. On passing ethylene through the solution, no obvious reaction was observed for one minute, after which a pronounced turbidity could be seen. After 10 minutes, the flask was opened, the contents diluted with ethanol and evaporated. The yield of polymer was 1.9 g.

EXAMPLE 21

In this example, ethylene was polymerized by reacting 69 mg of bis(cyclopentadienyl)hafnium dimethyl with 90 mg of N,N-dimethylanilinium bis(7,8-dicarbaundecaborato)cobaltate(III) in 50 ml of toluene in a septum-capped round bottomed flask. On passing ethylene through the solution, a pronounced turbidity appeared after 30 seconds as the solution grew hot. After 10 minutes, the solution was poured into acetone and the polymer filtered off and dried. The yield of linear polyethylene was 2.2 g.

EXAMPLE 22

In this example, ethylene was polymerized by reacting 50 mg of bis(trimethylsilylcyclopentadienyl)hafnium dimethyl with 45 mg of N,N-dimethylanilinium bis(7,8-dicarbaundecaborato) cobaltate(III) in 5 ml of toluene in a serum-capped vial. On passing ethylene through the solution, polymer formed as the mixture grew hot. After 1 minute, the vial was opened and the contents diluted with acetone and filtered off. The yield of linear polyethylene was 0.35 g.

EXAMPLE 23

In this example, ethylene and 1-butene were copolymerized in a toluene diluent by adding under a nitrogen atmosphere to a 1 liter stainless-steel autoclave, previously flushed with nitrogen and containing 400 ml of dry, oxygen-free toluene, 35 ml of a toluene solution containing a catalyst prepared in situ from 50 mg of bis(cyclopentadienyl)zirconium dimethyl and 45 mg of N,N-dimethylanilinium bis(7,8-dicarbaundecaborato)cobaltate(III). 1-Butene (200 ml) was added to the autoclave, which was further pressurized with 120 psig of ethylene. The autoclave was stirred at 50° for 30 minutes, then cooled and vented. The contents were dried under a stream of air. The weight of the polymer isolated was 44.7 g. The melting point of the polymer was 117° C. and analysis by infra-red spectroscopy indicated that there were about 17 ethyl branches per 1000 carbon atoms.

EXAMPLE 24

In this example, ethylene and 1-butene were copolymerized in a toluene diluent by adding under a nitrogen atmosphere to a 1 liter stainless-steel autoclave, previously flushed with nitrogen and containing 400 ml of dry, oxygen-free toluene, 50 ml of a catalyst solution in toluene containing 70 mg of bis(cyclopentadienyl)hafnium dimethyl and 45 mg of N,N-dimethylanilinium bis(7,8-dicarbaundecaborato)cobaltate(III). 1-Butene (200 ml) was added to the autoclave, which was further pressurized with 120 psig of ethylene. The autoclave was stirred at 50° for 20 minutes, then cooled and vented. The contents were dried under a stream of air. The yield of isolated polymer was 75.1 g. The melting point of the polymer was 109° C. and analysis by infra-red spectroscopy indicated that there were about 29 ethyl branches per 1000 carbon atoms.

EXAMPLE 25

In this example, ethylene was polymerized by reacting 66 mg of 1-bis(cyclopentadienyl)titana-3-dimethylsilacyclobutane and 88 mg of N,N-dimethylanilinium bis(7,8-dicarbaundecaborato) cotaltate(III) in 25 ml of toluene in a serum-capped round-bottomed flask. The solution darkened on passage of ethylene through it. After 10 minutes, the flask was opened and the contents diluted with ethanol. The polymer was filtered off, washed with ethanol and acetone, and dried. The yield of polyethylene isolated was 0.09 g.

EXAMPLE 26

In this example, ethylene was polymerized by reacting 61 mg of 1-bis(cyclopentadienyl)zircona-3-dimethylsilacyclobutane and 87 mg of N,N-dimethylanilinium bis(7,8-dicarbaundecaborato) cotaltate(III) in 20 ml of toluene in a serum-capped round-bottomed flask. On passing ethylene through the solution, polymer precipitated as the solution grew warm. After 10 minutes, the vial was opened and the contents diluted with ethanol. The precipitate was filtered off, washed with ethanol, and dried. The yield of polyethylene isolated was 1.41 g.

EXAMPLE 27

In this example, ethylene was polymerized by reacting 82 mg of 1-bis(cyclopentadlenyl)hafna-3-dimethylsllacyclobutane and 88 mg of N,N-dimethylanthinium bis(7,8-dicarbaundecaborato) cobaltate(III) in 20 ml of toluene in a serum-capped round-bottomed flask. On passing ethylene through the solution, polymer precipitated as the solution grew hot. After 5 minutes, the flask was opened and the contents diluted with ethanol. The polymer was filtered off, washed with ethanol, and dried. The yield of polyethylene isolated was 1.54 g.

EXAMPLE 28

In this example, ethylene was polymerized by reacting 67 mg of bis(cyclopentadienyl)zirconium(2,3-dimethyl-1,3-butadiene) and 88 mg of N,N-dimethylanilinium bis(7,8-dicarbaundecaborato) cobaltate(III) in 50 ml of toluene in a serum-capped bottle. Ethylene was passed through the solution, which gradually grew warm. After 15 minutes, the bottle was opened and the contents diluted with ethanol. The polymer was filtered off, washed with ethanol, and dried. The yield of polymer isolated was 1.67 g.

EXAMPLE 29

In this example, ethylene was polymerized by reacting 40 mg of bis(cyclopentadienyl)hafnium(2,3-dimethyl-1,3-butadiene) with 43 mg of N,N-dimethylanilinium bis(7,8-dicarbaundecaborato) cobaltate(III) in 50 ml of toluene in a serum-capped bottle. Ethylene was passed through the solution, which became turbid within 30 seconds. After 20 minutes, the bottle was opened and the contents diluted with ethanol. The solid polymer was filtered off, washed with ethanol, and dried. The yield of polyethylene isolated was 0.43 g.

EXAMPLE 30

In this example, ethylene was polymerized by reacting 55 mg of (pentamethylcyclopentadienyl) tetramethyl-eta 1-methylene -eta$^5$-cyclopentadienyl)zirconium phenyl and 45 mg of N,N-dimethylanilinium bis(7,8-dtcarbaundecaborato)cobaltate(III) in 20 ml of toluene in a serum-capped round-bottomed flask. On passing ethylene through the solution, polymer formed almost instantly and much heat was evolved. After 5 minutes, the flask was opened and the contents diluted with ethanol. The precipitate was filtered off, washed with acetone, and dried. The yield of polyethylene isolated was 0.55 g.

EXAMPLE 31

In this example, ethylene was polymerized by reacting 80 mg of (pentamethylcyclopentadienyl)(tetramethylcyclopentadienylmethylene)hafnium benzyl and 60 mg of N,N-dimethylanilinium bis<7,8-dicarbaundecaborato)cobaltate<III) in 50 ml of toluene in a serum-capped bottle. Ethylene was passed through the solution for 10 minutes. Polymer precipitated as the solution grew warm. The bottle was opened and the contents diluted with ethanol. The solid polymer was filtered off, washed with acetone, and dried. The yield of polyethylene isolated was 0.92 g.

EXAMPLE 32

In this example, ethylene was polymerized by reacting 0.42 g of bis(trimethylsilylcyclopentadienyl)hafnium dimethyl with 0.08 g N,N-dimethylanilinium bis(7,8-dicarbaundecaborato)cobaltate(III) in 10 ml of toluene. A portion of this solution (0.4 ml) was injected under a pressure of 3000 bar of Isopar into an autoclave pressurized to 1500 bar with ethylene and heated to 160°. After 5 seconds the contents of the autoclave were discharged. Linear polyethylene (2.1 g) with a weight-average molecular weight of 144,000 and a molecular weight distribution of 2.9 was isolated.

While the present invention has been described and illustrated by reference to particular embodiments thereof, it will be appreciated by those of ordinary skill in the art that the same lends itself to variations not necessarily illustrated herein. For this reason, then, reference should be made solely to the appended claims for purposes of determining the true scope of the present invention.

Having thus described and illustrated the invention, what is claimed is:

1. A method for polymerizing olefin, diolefin and/or acetylenically unsaturated monomers containing from 2 to about 18 carbon atoms either alone or in combination with one or more other monomers comprising:

(a) contacting at a temperature within the range from about −100° C. to about 300° C. and at a pressure within the range from about 0 to about 45,000 psig. said monomers in a suitable solvent or diluent with catalyst prepared by combining at least one first compound consisting of a bis(cyclopentadienyl) metal compound, said metal being selected from the Group consisting of titanium (Ti), zirconium (Zr) and hafnium (Hf), and at least one second compound comprising a cation capable of donating a proton to one or more substituents on said metal compound and a bulky, labile anion an ionic polymerization catalyst including a cation derived from a hydrolyzable bis(cyclopentadienyl) metal compound of a group IV-B metal, or a catalytically active decomposition product thereof, and a compatible noncoordinating anion comprising a plurality of boron atoms and sufficiently labile to permit displacement by an olefin and/or diolefin and/or acetylenically unsaturated monomer during polymerization;

(b) continuing the contacting of step (a) for a sufficient period of time to polymerize at least a portion of said monomers;

(c) recovering a polymer product.

2. The method of claim 1 wherein said olefin comprises one or more of the group consisting of ethylene, propylene and 1-butene.

3. The method of claim 2 wherein said olefin comprises ethylene.

4. The method of claim 2 wherein said temperature is between about 0° C. to about 160° C. and said pressure is between about 15 to about 500 psig.

5. The method of claim 3 wherein said temperature is between about 0° C. to about 160° C. and said pressure is between about 15 to about 500 psig.

6. The method of claim 1 wherein said ionic polymerization catalyst is represented by the formulae:

a) $[(A-Cp)MX_1]^+[B']^-$ or $[(A-Cp)MX_2]^+[B']^-$,

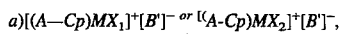

b) $[(A-Cp)MX'_1X'_2H]^+B'^-$ or $[(A-Cp)MX'_2X'_1H]^+[B']^-$, c) $[(A-Cp)M(LH)]^+[B']^-$, or d) $[(Cp)(HR-Cp^*)MX_1]^+[B']^-$ or $[(Cp)(R-Cp^*)M]^{+1}[B']^-$

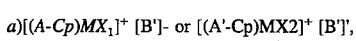

wherein

M is a metal selected from the Group consisting of titanium (Ti), zirconium (Zr) and hafnium (Hf);

(A-Cp) is either (Cp)(Cp*) or Cp-A'-Cp* and Cp and Cp* are the same or different substituted or unsubstituted cyclopentadienyl radicals, wherein A' is a covalent bridging group containing a Group IV-A element;

L is an olefin, diolefin or aryne ligand;

$X_1$ and $X_2$ are, independently, selected from the Group consisting of hydride radicals, hydrocarbyl radicals having from 1 to about 20 carbon atoms, substituted-hydrocarbyl radicals, wherein 1 or more of the hydrogen atoms are replaced with a halogen atom, having from 1 to about 20 carbon atoms, organo-metalloid radicals comprising a Group IV-A element wherein each of the hydrocarbyl substituents contained in the organo portion of said organo-metalloid, independently, contain from 1 to about 20 carbon atoms;

$X'_1$ and $X'_2$ form a hydrocarbocyclic ring containing from about 3 to about 20 carbon atoms; and R is a substituent on one of the cyclopentadienyl radicals which is also bound to the metal atom.

7. The method of claim 6 wherein at least one of Cp and Cp* is substituted with at least one hydrocarbyl radical containing from 1 to about 20 carbon atoms.

8. The method of claim 7 wherein said olefin comprises ethylene.

9. The method of claim 7 wherein said hydrocarbyl radical is selected from the group consisting of straight and branched alkyl radicals, cyclic hydrocarbon radicals, alkyl-substituted cyclic hydrocarbon radicals, aromatic radicals, and alkyl-substituted aromatic radicals.

10. The method of claim 9 wherein said radicals include indenyl.

11. The method of claim 9 wherein said ionic polymerization catalyst is represented by the formulae:

a) $[(A-Cp)MX_1]^+$ [B']- or $[(A'-Cp)MX2]^+$ [B']', wherein (A-Cp) is (Cp-A-Cp*), M is zirconium or hafnium, and $X_1$ and $X_2$ are independently hydride or methyl.

12. The method of claim 11 wherein said olefin comprises ethylene.

13. The method of claim 11 wherein said olefin comprises propylene.

14. The method of claim 6 wherein said noncoordinating anion [B']− comprises a salt or complex selected from the group consisting of borate, carborate, borane, carborane, metallaborane and metallacarborane salts and complexes.

15. The method of claim 14 wherein said noncoordinating anion [B']− comprises salt of a borates or carborates.

16. The method of claim 14 wherein said noncoordinating anion [B']− comprises nonaborate, undecaborate, 1-carbadodecaborate, 1-carbaundecaborate, decachloroborate, or dodecachlorododecaborate.

17. The method of claim 14 wherein said noncoordinating anion [B']− comprises a salt or complex of boranes or carboranes.

18. The method of claim 14 wherein said noncoordinating anion [B']⁻ comprises a salt of a metallaboranes or metallacarboranes.

19. The method of claim 11 wherein said noncoordinating anion [B']⁻ comprises a salt or complex selected from the group consisting of borate, carborate, borane, carborane, metallaborane and metallacarborane salts and complexes.

20. The method of claim 19 wherein said noncoordinating anion [B']⁻ is nonaborate, undecaborate, 1-carbadodecaborate, 1-carbaundecaborate, decachloroborate, or dodecachlorododecaborate.

* * * * *

UNITED STATES PATENT AND TRADEMARK OFFICE
CERTIFICATE OF CORRECTION

PATENT NO. : 5,483,014
DATED : January 9, 1996
INVENTOR(S) : Turner et al

It is certified that error appears in the above-indentified patent and that said Letters Patent is hereby corrected as shown below:

In Claim 1, Column 21, Lines 33 - 40, delete the phrase "catalyst prepared by combining at least one first compound consisting of a bis(cyclopentadienyl) metal compound, said metal being selected from the Group consisting titanium (Ti), zirconium (Zr) and hafnium(Hf), and at least one second compound comprising a cation capable of donating a proton to one or more substituents on said metal compound and a bulky, labile anion".

In the specification in Column 7, Line 30, replace

"5. $[L'-H]C+[(CX)_a(BX')_m X''_b]^{c-}$"

with :

—5. $[L-H]_{c+}[(CX)_a(BX')_m X''_b]^c$—.

In the specification in Column 7, Line 61, replace

"6. $[L'-H]C^+[[[(CX_3)_a(BX_4)_m(X_5)_b]^{c-}]_2 M^{n+}]^{d-}$ with:

—6. $[L'H]_{c+} [[[(CX_3)_a(BX_4)_m(X_5)_b]^{c-}]_2 M^{n+}]^{d-}$—.

Signed and Sealed this

Twenty-second Day of October, 1996

Attest:

BRUCE LEHMAN

*Attesting Officer*  *Commissioner of Patents and Trademarks*